US008540667B2

(12) United States Patent
Gerrans et al.

(10) Patent No.: US 8,540,667 B2
(45) Date of Patent: Sep. 24, 2013

(54) MULTI-BALLOON CATHETER FOR EXTRAVASATED DRUG DELIVERY

(75) Inventors: Lawrence J. Gerrans, San Anselmo, CA (US); Erhan H. Gunday, Great Neck, NY (US)

(73) Assignee: Sanovas, Inc., Sausalito, CA (US)

( * ) Notice: Subject to any disclaimer, the term of this patent is extended or adjusted under 35 U.S.C. 154(b) by 0 days.

(21) Appl. No.: 13/042,901

(22) Filed: Mar. 8, 2011

(65) Prior Publication Data

US 2011/0218494 A1    Sep. 8, 2011

(51) Int. Cl.
*A61M 29/00*    (2006.01)

(52) U.S. Cl.
USPC ...................................... 604/96.01

(58) Field of Classification Search
USPC ...................................... 604/96.01
See application file for complete search history.

(56) References Cited

U.S. PATENT DOCUMENTS

| | | | |
|---|---|---|---|
| 3,720,199 A * | 3/1973 | Rishton et al. ............. | 600/18 |
| 4,186,745 A | 2/1980 | Lewis et al. | |
| 4,423,725 A | 1/1984 | Baran et al. | |
| 4,446,867 A | 5/1984 | Leveen et al. | |
| 4,636,195 A | 1/1987 | Wolinsky | |
| 4,773,899 A | 9/1988 | Spears | |
| 4,824,436 A | 4/1989 | Wolinsky | |
| 4,921,484 A | 5/1990 | Hillstead | |
| 4,994,033 A | 2/1991 | Shockey et al. | |
| 5,049,132 A | 9/1991 | Shaffer et al. | |
| 5,100,425 A | 3/1992 | Fischell et al. | |
| 5,196,017 A | 3/1993 | Silva et al. | |
| 5,304,121 A | 4/1994 | Sahatjian | |
| 5,336,234 A | 8/1994 | Vigil et al. | |
| 5,397,307 A | 3/1995 | Goodin | |
| 5,423,745 A | 6/1995 | Todd et al. | |
| 5,545,133 A | 8/1996 | Burns et al. | |

(Continued)

FOREIGN PATENT DOCUMENTS

| | | |
|---|---|---|
| EP | 0894507 A2 | 2/1999 |
| EP | 1913882 A1 | 4/2008 |

(Continued)

OTHER PUBLICATIONS

Altinoz et al., "Noscapine and diltiazem augment taxol and radiation-induced S-phase arrest and clonogenic death of C6 glioma in vitro", May 2006, Surgical Neurology, 65(5):478-84.*

(Continued)

*Primary Examiner* — Jason Flick
(74) *Attorney, Agent, or Firm* — St. Onge Steward Johnston & Reens LLC

(57) ABSTRACT

A method of extravasated delivery of a therapeutic and/or diagnostic agent to tissue is provided including inserting a catheter with a first balloon, a second balloon and a third balloon into a bodily cavity, inflating the first and second balloons by supplying fluid thereto to create a chamber, delivering the agent to the chamber, and increasing fluid pressure within the chamber by inflating the third balloon to facilitate extravasation of the agent into tissue. A multi-balloon catheter system is also provided including a catheter having a first balloon, a second balloon and a third balloon, and a fluid source that inflates the first and second balloons by supplying fluid thereto to create a chamber, wherein the catheter includes a fluid pathway for delivering the agent, and the fluid source increases fluid pressure within the chamber by supplying fluid to the third balloon such that the agent is extravasated into tissue.

24 Claims, 12 Drawing Sheets

(56) References Cited

U.S. PATENT DOCUMENTS

| | | | |
|---|---|---|---|
| 5,599,307 A | 2/1997 | Bacher et al. | |
| 5,611,775 A | 3/1997 | Machold et al. | |
| 5,647,847 A | 7/1997 | Lafontaine et al. | |
| 5,674,192 A | 10/1997 | Sahatjian et al. | |
| 5,707,352 A | 1/1998 | Sekins et al. | |
| 5,728,064 A | 3/1998 | Burns et al. | |
| 5,785,685 A | 7/1998 | Kugler et al. | |
| 5,833,644 A | 11/1998 | Zadno-Azizi et al. | |
| 5,868,708 A * | 2/1999 | Hart et al. | 604/104 |
| 5,873,852 A | 2/1999 | Vigil et al. | |
| 5,932,248 A | 8/1999 | Chen et al. | |
| 6,048,332 A | 4/2000 | Duffy et al. | |
| 6,129,705 A | 10/2000 | Grantz | |
| 6,149,596 A | 11/2000 | Bancroft | |
| 6,190,354 B1 | 2/2001 | Sell et al. | |
| 6,245,008 B1 | 6/2001 | Leschinsky et al. | |
| 6,248,092 B1 | 6/2001 | Miraki et al. | |
| 6,485,500 B1 | 11/2002 | Kokish et al. | |
| 6,544,221 B1 | 4/2003 | Kokish et al. | |
| 6,616,597 B2 | 9/2003 | Schock et al. | |
| 6,623,452 B2 | 9/2003 | Chien et al. | |
| 6,685,648 B2 | 2/2004 | Flaherty et al. | |
| 6,733,459 B1 | 5/2004 | Atsumi | |
| 7,014,652 B2 | 3/2006 | Cioanta et al. | |
| 7,025,718 B2 | 4/2006 | Williams | |
| 7,047,058 B1 | 5/2006 | Dvorsky et al. | |
| 7,462,165 B2 | 12/2008 | Ding et al. | |
| 7,569,032 B2 | 8/2009 | Naimark et al. | |
| 7,611,484 B2 * | 11/2009 | Wellman et al. | 604/103.08 |
| 7,658,966 B2 | 2/2010 | Kokish | |
| 7,727,226 B2 | 6/2010 | Chang et al. | |
| 8,052,668 B2 * | 11/2011 | Sih | 604/509 |
| 2002/0010418 A1 | 1/2002 | Lary et al. | |
| 2003/0114791 A1 * | 6/2003 | Rosenthal et al. | 604/96.01 |
| 2004/0059290 A1 | 3/2004 | Palasis | |
| 2004/0215140 A1 | 10/2004 | Forman | |
| 2005/0015049 A1 | 1/2005 | Rioux et al. | |
| 2006/0135984 A1 * | 6/2006 | Kramer et al. | 606/192 |
| 2006/0189930 A1 * | 8/2006 | Lary et al. | 604/101.01 |
| 2007/0027075 A1 * | 2/2007 | Smithrud | 514/12 |
| 2007/0060942 A2 * | 3/2007 | Zadno-Azizi | 606/194 |
| 2007/0073264 A1 * | 3/2007 | Stedman et al. | 604/500 |
| 2008/0039791 A1 | 2/2008 | Abboud et al. | |
| 2008/0051627 A1 | 2/2008 | Raju | |
| 2008/0171985 A1 | 7/2008 | Karakoca | |
| 2008/0208118 A1 * | 8/2008 | Goldman | 604/103.01 |
| 2008/0300571 A1 * | 12/2008 | LePivert | 604/503 |
| 2009/0229374 A1 | 9/2009 | Carlisle et al. | |
| 2010/0074895 A1 * | 3/2010 | Petricoin et al. | 424/133.1 |
| 2010/0113939 A1 | 5/2010 | Mashimo et al. | |
| 2010/0121270 A1 | 5/2010 | Gunday et al. | |
| 2010/0145398 A1 | 6/2010 | Li et al. | |
| 2010/0280451 A1 | 11/2010 | Teeslink et al. | |
| 2010/0286467 A1 | 11/2010 | Pesach et al. | |
| 2011/0082427 A1 * | 4/2011 | Golzarian et al. | 604/187 |
| 2011/0293629 A1 * | 12/2011 | Bastid et al. | 424/158.1 |

FOREIGN PATENT DOCUMENTS

| | | |
|---|---|---|
| WO | 9304727 A1 | 3/1993 |
| WO | 2006130326 A2 | 12/2006 |
| WO | 2009046206 A1 | 4/2009 |
| WO | 2009086269 A2 | 7/2009 |

OTHER PUBLICATIONS

International Search Report and Written Opinion of the International Searching Authority; PCT/US2010/034689; Jul. 15, 2010; 10 pages.

European Search Report; Application No. EP 12 15 8147; Issued: Jun. 6, 2012; 6 pages.

* cited by examiner

MULTI-BALLOON CATHETER FOR EXTRAVASATED DRUG DELIVERY

FIELD OF THE INVENTION

The present invention relates to methods and systems for delivering therapeutic and diagnostic agents to specific cellular locations within and adjacent to bodily tissues and cavities. More specifically, the invention relates to a system and method of extravasated delivery of diagnostic and/or therapeutic agents to bodily tissues and cavities via a multi-balloon catheter that facilitates extravasation of the agent into cellular membranes and structural walls of bodily cavities.

BACKGROUND OF THE INVENTION

In diagnosing and treating diseases of various body cavities and organs, it is necessary to deliver diagnostic and/or therapeutic agents to the organs at specified locations. Most common routes of drug delivery include a non-invasive peroral (through the mouth), topical (skin), transmucosal (nasal, buccal/sublingual, vaginal, ocular and rectal) and inhalation routes. However, many therapeutic and diagnostic agents in general may not be delivered using these routes because they might be susceptible to enzymatic degradation or cannot be absorbed into the systemic circulation efficiently due to molecular size and charge issues, and thus, will not be therapeutically effective. For this reason, many such drugs have to be delivered by injection.

There are several known problems associated with the injection process. One of such problems is undesirable extravasation of the diagnostic or therapeutic agents into tissue, which is particularly prevalent with intravenously injected agents. Extravasation generally refers to leakage of fluids out of a container, and more specifically refers to leakage of intravenous drugs from a vein into surrounding tissues, resulting in an injury to the tissues. Once the intravenous extravasation has occurred, damage can continue for months and involve nerves, tendons and joints. If treatment is delayed, surgical debridement, skin grafting, and even amputation have been known to be the unfortunate consequences.

Occurrence of extravasation is possible with all intravenous drugs, but it is a particularly significant problem with cytoxic drugs used for treatment of cancer (i.e. during chemotherapy).

Chemotherapy is the general term for any treatment involving the use of chemical agents to stop cancer cells from growing. Chemotherapy can eliminate cancer cells at sites great distances from the original cancer. As a result, chemotherapy is considered a systemic treatment. More than half of all people diagnosed with cancer receive chemotherapy. A chemotherapy regimen (a treatment plan and schedule) usually includes drugs to fight cancer plus drugs to help support completion of the cancer treatment.

Chemotherapy can be administered through a vein, injected into a body cavity, or delivered orally in the form of a pill, depending on which drug is used. Chemotherapy works by destroying cancer cells. Unfortunately, it cannot tell the difference between a cancer cell and some healthy cells. Thus, chemotherapy often eliminates not only the fast-growing cancer cells, but also other fast-growing cells in the body, including hair and blood cells. Some cancer cells grow slowly while others grow rapidly. As a result, different types of chemotherapy drugs target the growth patterns of specific types of cancer cells.

Each chemotherapy drug works differently and is effective at a specific time in a life cycle of the cell it targets. Brachytherapy, sometimes called seed implantation, is an outpatient procedure used in the treatment of different kinds of cancer. The radioactive "seeds" are carefully placed inside of the cancerous tissue and positioned in a manner that will attack the cancer most efficiently. The radioactive seeds are about the size of a grain of rice, and give off radiation that travels only a few millimeters to kill nearby cancer cells. There are two different kinds of brachytherapy: permanent, when the seeds remain inside the body, and temporary, when the seeds are inside of the body and are then removed. With permanent implants (e.g. prostate), the radioactivity of the seeds typically decays with time.

The other type of chemotherapy is when cytotoxic agents are delivered intravenously. Veins of people receiving chemotherapy are often fragile, mobile, and difficult to cannulate. Patients who receive chemotherapy at the same site as radiotherapy may experience a reactivation of skin toxicity known as a "recall" phenomenon. Patients who have had previous radiation therapy at the site of injection may develop severe local reactions from cytotoxic drugs. Cytotoxic drugs also have the potential to cause cutaneous abnormalities in areas that have been damaged previously by radiation, even in areas that are distant from the injection site. Patients who receive further chemotherapy in a different site may experience an exacerbation of tissue damage in the original site.

Furthermore, areas of previous surgery where the underlying tissue is likely to be fibrosed and toughened dramatically present an increased risk of extravasation. Radical mastectomy, axillary surgery or lymph node dissection may impair circulation in a particular limb. This reduces venous flow and may allow intravenous solutions to pool and leak around the site of cannulation.

Some chemotherapy drugs often never reach the tumors they are intended to treat because the blood vessels feeding the tumors are abnormal. A tumor's capillaries (small blood vessels that directly deliver oxygen and nutrients to cancer cells) can be irregularly shaped, being excessively thin in some areas and forming thick, snarly clumps in others. These malformations create a turbulent, uneven blood flow, so that too much blood goes to one region of the tumor, and too little to another. In addition, the capillary endothelial cells lining the inner surface of tumor capillaries, normally a smooth, tightly-packed sheet, have gaps between them, causing vessel leakiness.

The systemic and intravenous side effects of chemotherapy coupled with the limited effect of systemic administration due to abnormal characteristics of tumor blood vessels have given the scientific community pause, in searching for more direct, localized and biologic solutions. Accordingly, the oncology literature has become increasingly populated with articles espousing prospective benefits and positive outcomes of intra-tumoral chemotherapy. A direct administration of cytotoxic drugs such as Mytomycin, Mytomycin-C, Bleomycin, Fluorouracil, Mitoxantrone, Cisplatin, and Avastin in endobronchial intra-tumoral chemotherapy has been done experimentally via direct injection of the agent into the endobronchial tumor. In these cases, the tumor was reported to have died and been subsequently removed.

However, while some experimental uses of the localized delivery of cytotoxic drugs have been attempted, there has been little implementation of such drug delivery in practice, possibly due to numerous problems associated with such delivery. First, it is often necessary to deliver cytotoxic drugs to remote and not easily accessible blood vessels and other lumens within body organs, such as lungs. It is also important to be able to deliver defined doses of the cytotoxic substances because such substances are often very expensive or are capable of causing serious harm if delivered in excess. Moreover, the existing methods lack the ability to contain the cytotoxic agent and/or radiation therapy and mitigate collateral damage to non-affected anatomy and structures.

Several devices have been proposed for a targeted delivery of drugs to internal bodily cavities. For example, U.S. Pat. No. 4,824,436 to Wolinsky discloses a catheter system for delivery of heparin or other SMC growth regulators to the site of angioplasty. The catheter includes a main catheter body held in place by the inflation of two spaced balloons, which form a chamber therebetween. Heparin is delivered to the chamber between the balloons and is absorbed into the surrounding tissue. The catheter also includes a central balloon, which is used to rupture the plague in an artery.

U.S. Pat. No. 7,611,484 to Wellman et al. discloses a multi-balloon catheter designed for treatment of deceased blood vessels, and specifically lesions in the blood vessels. The catheter includes a pair of end balloons that, when inflated, isolate the deceased region of the blood vessel. The catheter further includes a middle balloon having an outer wall with a plurality of micro-needles that enable the therapeutic agents to be injected into the blood vessel wall.

U.S. Pat. No. 6,485,500 to Kokish et al. discloses a system for isolation of a section of a blood vessel to prevent migration of emboli from the section during an intervention procedure, and subsequent flushing of the section to remove any emboli dislodged during the procedure. The system includes distal and proximal blocking balloons for isolating a portion of a blood vessel and for delivering flushing fluid through perforations in the balloons. The system can also be provided with a third balloon positioned between the distal and proximal balloons for delivering a stent device.

While the above described catheter devices are useful for delivering the drugs to a specific target site, these systems are not particularly efficient at infusing the relevant biological material with the drug. Instead, the catheter may need to remain in place for an unnecessarily long period of time while the infusion of the drug into the biological material is allowed to take place. This is undesirable, especially in applications such as pulmonology, where the patient's respiratory passage has been somewhat restricted by the device. Further, this can result in some of the agent never being infused into the targeted material and instead remaining in the cavity and, after the balloon catheter is removed, subsequently migrating to other undesired portions of the body.

What is desired, therefore, is a balloon catheter system for delivering therapeutic and/or diagnostic agents to bodily tissues, tumors, and other biological materials that can locally deliver the agent to a specific target site. What is further desired is a balloon catheter system for delivering therapeutic and/or diagnostic agents that facilitates the infusion of the drug into surrounding bodily tissues, tumors, and other biological materials. What is also desired is a balloon catheter system for delivering therapeutic and/or diagnostic agents that can adjust for changing conditions during the process of delivering the drug. What is also desired is a balloon catheter system that maintains and facilitates the vital functionality of the vessel under treatment.

SUMMARY OF THE INVENTION

Accordingly, it is an object of the present invention to provide a multi-balloon catheter system that can deliver therapeutic and/or diagnostic agents to bodily tissues, tumors, and other biological materials from within bodily cavities.

It is a further object of the present invention to provide a multi-balloon catheter system that can target specific areas for the delivery of therapeutic and/or diagnostic agents to bodily tissues, tumors, and other biological materials.

It is yet another object of the present invention to provide a multi-balloon catheter system that facilitates extravasation of therapeutic and/or diagnostic agents into surrounding bodily tissues, tumors, and other biological materials.

It is another object of the present invention to provide a multi-balloon catheter system for delivering therapeutic and/or diagnostic agents to bodily tissues, tumors, and other biological materials that permits the passage of bodily fluids through the system.

It is yet another object of the present invention to provide a multi-balloon catheter system for delivering therapeutic and/or diagnostic agents to bodily tissues, tumors, and other biological material that provides visualization from within the bodily cavity.

In order to overcome the deficiencies of the prior art and to achieve at least some of the objects and advantages listed, the invention comprises a method of extravasated delivery of a therapeutic and/or diagnostic agent to tissue, including the steps of inserting a catheter into a bodily cavity, the catheter comprising a first balloon, a second balloon, and a third balloon positioned between the first and second balloons, inflating the first and second balloons to create a chamber between the first balloon and the second balloon, delivering the therapeutic and/or diagnostic agent to the chamber, and facilitating extravasation of the agent into tissue by repeatedly increasing and decreasing fluid pressure within the chamber by at least partially inflating and at least partially deflating the third balloon.

A method of extravasated delivery of a therapeutic and/or diagnostic agent to tissue is also provided, comprising the steps of inserting a catheter into a bodily cavity, the catheter including a first balloon, a second balloon, and a third balloon positioned between the first and second balloons, inflating the first and second balloons by supplying fluid thereto to create a chamber between the first balloon and the second balloon, delivering the therapeutic and/or diagnostic agent to the chamber, and increasing fluid pressure within the chamber by at least partially inflating the third balloon by supplying fluid thereto to facilitate extravasation of the agent into tissue in the bodily cavity.

In some embodiments, the method also includes the step of decreasing the fluid pressure within the chamber by at least partially deflating the third balloon. In some of these embodiments, the method further includes repeating the steps of increasing and decreasing the fluid pressure within the chamber.

In certain embodiments, the third balloon has a wall with an abrasive outer surface, and the method further includes the step of abrading tissue in the bodily cavity by contacting the tissue with the abrasive surface when the third balloon is inflated.

In some embodiments, the first balloon and the second balloon each have a wall with a textured outer surface, and the step of inflating the first and second balloons further comprises contacting tissue in the bodily cavity with the textured surface to prevent slippage of the surface on the tissue.

In certain advantageous embodiments, the steps of inflating the first balloon, the second balloon and the third balloon comprise supplying fluid to each of the first, second and third balloons with an electro-pneumatic pump.

In certain embodiments, the method further includes monitoring at least one vital sign of a patient.

In some cases, the method further includes the step of providing a vacuum to evacuate at least some of the agent from the chamber.

In certain embodiments, the step of delivering the therapeutic and/or diagnostic agent comprises delivering the agent to the chamber through at least one opening in the catheter. In other embodiments, the step of delivering the therapeutic and/or diagnostic agent comprises delivering the agent through at least one opening in at least one of the wall of the first balloon, the wall of the second balloon and the wall of the third balloon. In yet other embodiments, the step of delivering the therapeutic and/or diagnostic agent comprises inflating the third balloon until an outer surface of the third balloon contacts tissue in the bodily cavity.

In some embodiments, the method further includes the step of circulating the therapeutic agent within the chamber, wherein the agent enters the chamber through a first opening in the catheter positioned on one side of the third balloon and exits the chamber through a second opening in the catheter positioned on the other side of the third balloon.

In certain embodiments, the method further includes the step of using an imaging device disposed in the catheter to visualize tissue in the bodily cavity.

In some advantageous embodiments, the method also includes the step of measuring at least one characteristic of tissue in the bodily cavity via at least one sensor. In additional advantageous embodiments, the fluid is a gas.

In some embodiments, the agent is doxorubicin. In other embodiments, the agent is cisplatin, and the method further includes the step of supplying a second agent, the second agent being epinephrine. In further embodiments, the agent is 5-4 fluorouracil. In some embodiments, the agent is noscapine, and in some cases, the agent is diltiazem augment taxol. In other embodiments, the agent is crizotinib, gefitinib, or erlotinib hydrochloride. In some embodiments, the agent includes drug eluting microspheres, which in some cases, contain doxorubicin. In yet further embodiments, the agent is a combination of at least one therapeutic agent and at least one biomarker, and the method further includes the step of monitoring extravasation of the at least one therapeutic agent into tissue via the at least one biomarker. In some of these embodiments, the biomarker is a radio-opaque marker.

In some embodiments, a distal end of the catheter has an opening therein, and the method further includes the step of passing bodily fluids through a lumen in the catheter via the opening. In some of these embodiments, the method further includes using an external device to urge the bodily fluids through the lumen.

In certain embodiments, the catheter further includes a fourth balloon, and the method further includes the step of inflating the fourth balloon by supplying fluid thereto to create a chamber between the first balloon, the second balloon and the fourth balloon, and to secure the catheter in the bodily cavity. In certain of these embodiments, the catheter includes a first catheter section connecting the first balloon and the third balloon, a second catheter section connecting the second balloon and the third balloon, and a third catheter section connecting the fourth balloon and the third balloon, wherein the first, second, and third catheter sections are interconnected inside the third balloon. In some of these embodiments, the step of inserting the catheter into the bodily cavity includes increasing a distance between the second and third catheter sections by at least partially inflating the third balloon to insert the second and third catheter sections into different portions of the bodily cavity.

A multi-balloon catheter system for delivering a therapeutic and/or diagnostic agent to tissue is also provided including a catheter having a first balloon, a second balloon, and a third balloon positioned between the first and second balloons, an a fluid source that inflates the first and second balloons by supplying fluid thereto to create a chamber between the first balloon and the second balloon, wherein the catheter has a fluid pathway for delivering the therapeutic and/or diagnostic agent to the chamber, and wherein the fluid source increases fluid pressure within the chamber by supplying fluid to the third balloon such that the agent is extravasated into tissue.

In some embodiments, the fluid source is an electro-pneumatic pump. In certain of these embodiments, the pump supplies fluid to the third balloon in pulsed fashion to repeatedly inflate and deflate the third balloon. In other embodiments, the fluid source further includes a vacuum source that evacuates fluid from at least one of the first balloon, the second balloon and the third balloon.

In certain embodiments, the invention further includes a monitoring device for monitoring at least one patient vital sign, and the pump controls the pressure to which the inner balloon is inflated based at least in part on the monitored vital sign. In some embodiments, the invention includes a monitoring device for monitoring at least one patient vital sign, and the pump controls the supply of the therapeutic and/or diagnostic agent based at least in part on the monitored vital sign.

In certain embodiments, the first balloon and the second balloon each have a wall with a textured outer surface for preventing slippage of the outer surface on tissue in a bodily cavity.

In some advantageous embodiments, the fluid pathway includes at least one opening in the catheter, positioned between the first balloon and the second balloon and in fluid communication with a lumen in the catheter for supplying the therapeutic and/or diagnostic agent to the chamber. In other advantageous embodiments, the fluid pathway includes at least one opening in a wall of at least one of the first balloon, the second balloon and the third balloon, and the at least one opening is in fluid communication with a lumen in the catheter for supplying the therapeutic and/or diagnostic agent to the chamber.

In certain embodiments, the third balloon has a wall with an abrasive outer surface for abrading tissue in a bodily cavity for stimulating a flow of blood cells to the tissue. In some cases, the outer surface comprises a mesh sleeve that is radiopaque. In some embodiments, the abrasive outer surface of the third balloon comprises a mesh molded into the wall of the balloon.

In some cases, the multi-balloon catheter system further includes an imaging device disposed in the catheter for viewing tissue in the bodily cavity.

In some embodiments, the multi-balloon catheter system also includes at least one imaging marker mounted adjacent to at least one of the first balloon, the second balloon and the third balloon. In certain advantageous embodiments, the imaging marker is radiopaque.

In certain embodiments, the fluid is a gas.

In some cases, a distal end of the catheter has an opening therein, and the catheter has a lumen in fluid communication with the opening for passing bodily fluids therethrough.

In certain embodiments, the multi-balloon catheter system further includes a fourth balloon fluidly connected to a lumen, wherein the lumen is connected to the catheter between the first balloon and the third balloon, and wherein the fluid source inflates the fourth balloon via the lumen to create a chamber between the first, second and fourth balloons.

Other objects of the invention and its particular features and advantages will become more apparent from consideration of the following drawings and accompanying detailed description.

DETAILED DESCRIPTION OF THE INVENTION

Figure 1:
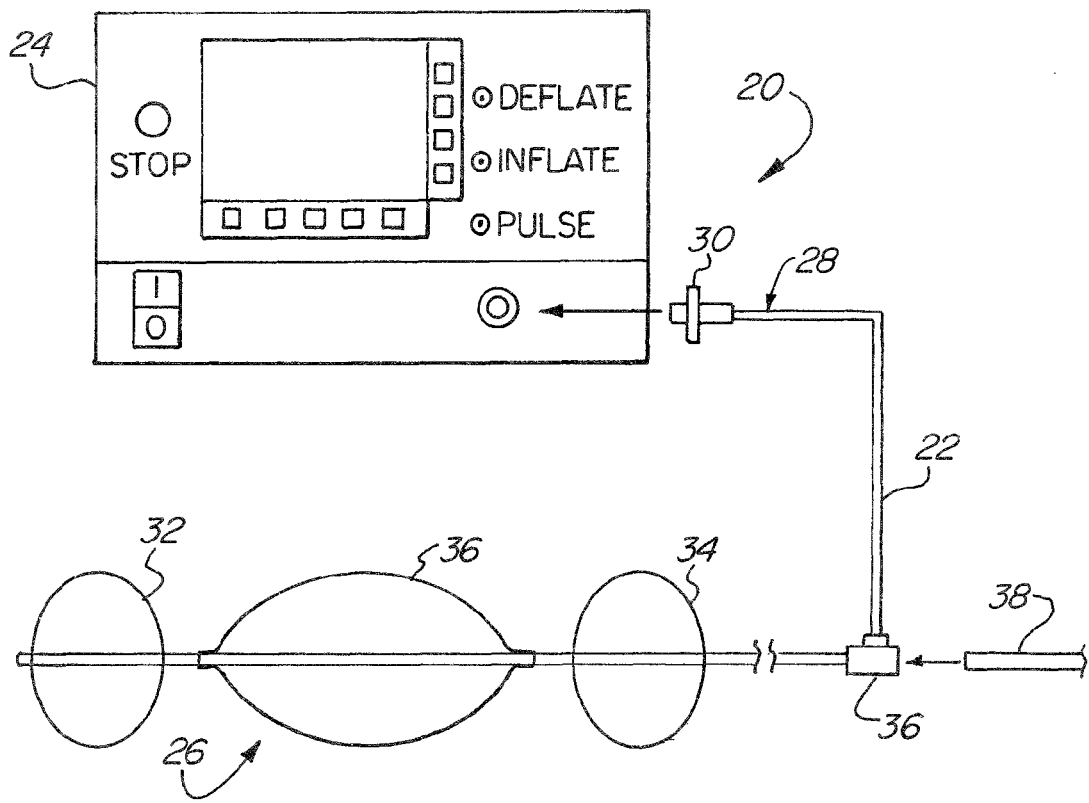
FIG. 1 is a schematic view of a multi-balloon catheter system for delivering therapeutic and/or diagnostic agents in accordance with the invention.

The basic components of one embodiment of a multi-balloon catheter system in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

As shown in FIG. 1, the multi-balloon catheter system (20) includes a catheter (22) and a fluid source (24). The catheter (22) may have any suitable diameter and length depending on a particular application, and may be flexible, rigid or semi rigid. The catheter (22) may be made with any commercially available material, such as polyethylene, that is flexible enough to allow the shaft to be safely inserted through the available opening of a bodily cavity such that it will bend instead of puncturing the walls of the cavity, and at the same time is rigid enough such as it will maintain its shape as it is passed alongside and/or through the available opening of the bodily cavity. In an advantageous embodiment, the catheter (22) consists of a coil wire made of any suitable material, such as stainless steel, and a coating made of polyethylene. A distal end of the catheter (22) preferably includes a safety tip (not shown) that, when the catheter (22) is inserted into a bodily cavity, will bend instead of puncturing the walls of the cavity.

Any suitable fluid source may be used in accordance with the present invention. In the preferred embodiment shown in FIG. 1, the fluid source (24) is an electro-pneumatic pump having controls on the front thereof, from which a physician or assistant can control the system (as well as a remote control unit), such as that disclosed in U.S. Patent Application No. 2010/0121270 by Gunday et al., the specification of which is hereby incorporated by reference herein in its entirety. A proximal end (28) of the catheter (22) is connected to the pump (24) via a connection (30). The connection (30) may comprise any suitable connector, such as a luer connector, for connection to the pump. The pump (24) supplies a fluid, such as a gas, liquid, or mixture thereof, to the catheter (22). The pump (24) also includes a variety of capabilities for balloon identification, proper inflation/deflation of the balloons, and feedback measurements, many details of which are described in Gunday et al. In certain advantageous embodiments, the pump (24) further includes a vacuum source to evacuate fluid from the catheter (22).

In some embodiments, the catheter (22) includes a data device, which may, for example, be optical, RFID, flash memory, etc. As a result, the pump (24) is able to identify the type of catheter that is connected and read catheter characterization data (including pressure, volume, dimensions, etc.) included thereon, and then adjust its control accordingly based on user input.

The pump (24) also controls and regulates the pressure by monitoring and taking into account one or more vital signs of the patient, such as body temperature, heart rate, blood pressure, and respiratory rate. For example, in certain applications, it will be desirable to know the degree to which the lung is inflated at any given time in order to deliver a therapeutic and/or diagnostic agent at the right time. Similarly, in certain cases, it will be important to measure the systolic and diastolic blood pressure, and at appropriate times, apply a pressure that exceeds the systolic pressure in order to facilitate extravasation of an agent. In certain embodiments, the electro-pneumatic pump (24) interfaces with an external monitoring device to obtain and monitor the patient vital signs to control the applied balloon pressure and/or the timing of the drug delivery. In other cases, the monitoring device is located in the pump (24).

In an advantageous embodiment, the catheter (22) also includes a connection port (36) for insertion of an imaging device (38). The structure and operation of the imaging device is described in more detail below.

The multi-balloon catheter system (20) also includes a plurality of inflatable balloons positioned at a distal end (26) of the catheter (22). As shown in FIG. 1, the plurality of balloons comprises a first balloon (32), a second balloon (34) and a third balloon (36), positioned between the first and second balloons (32, 34). The balloons (32, 34, 36) may be made of latex, Yulex, polyethylene, nylon or other suitable material, and may come in a variety of sizes and diameters, which allow the multi-balloon catheter system (20) to be used in bodily cavities of various diameters and dimensions, such as large and small bronchial branches, sinuses, and blood vessels, having different types of tumors and tissues to be treated.

Figure 2:
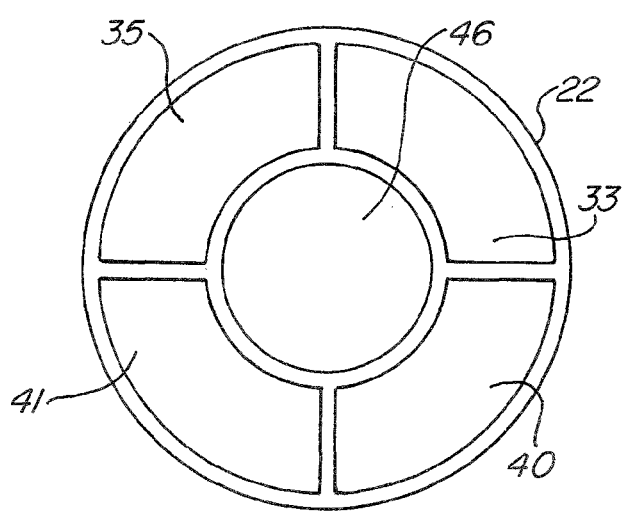
FIG. 2 is a cross-sectional view of the catheter system of FIG. 1.
Figure 3:
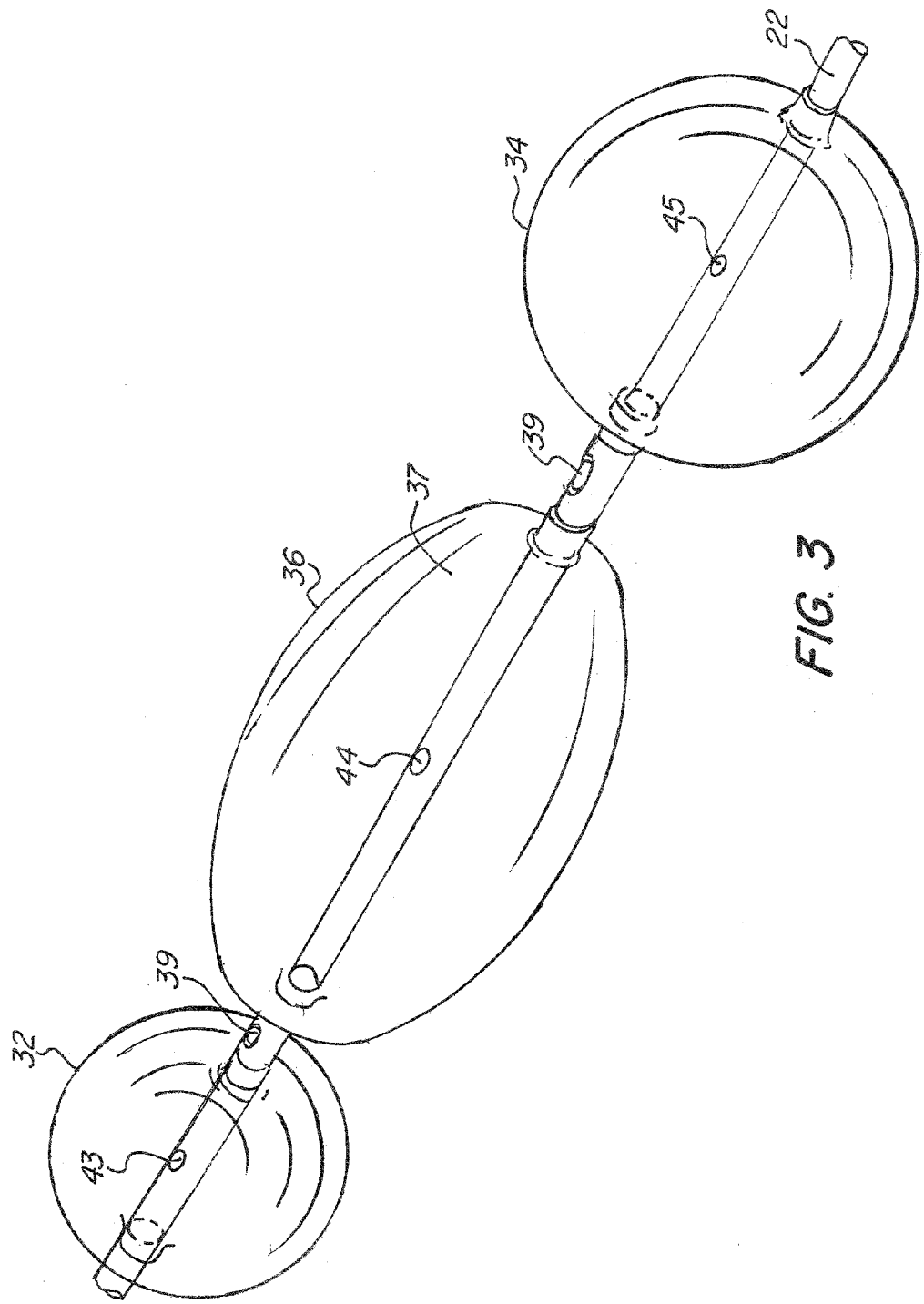
FIG. 3 is an enlarged perspective view of the multi-balloon construct of the catheter system of FIG. 1.
Figure 5:
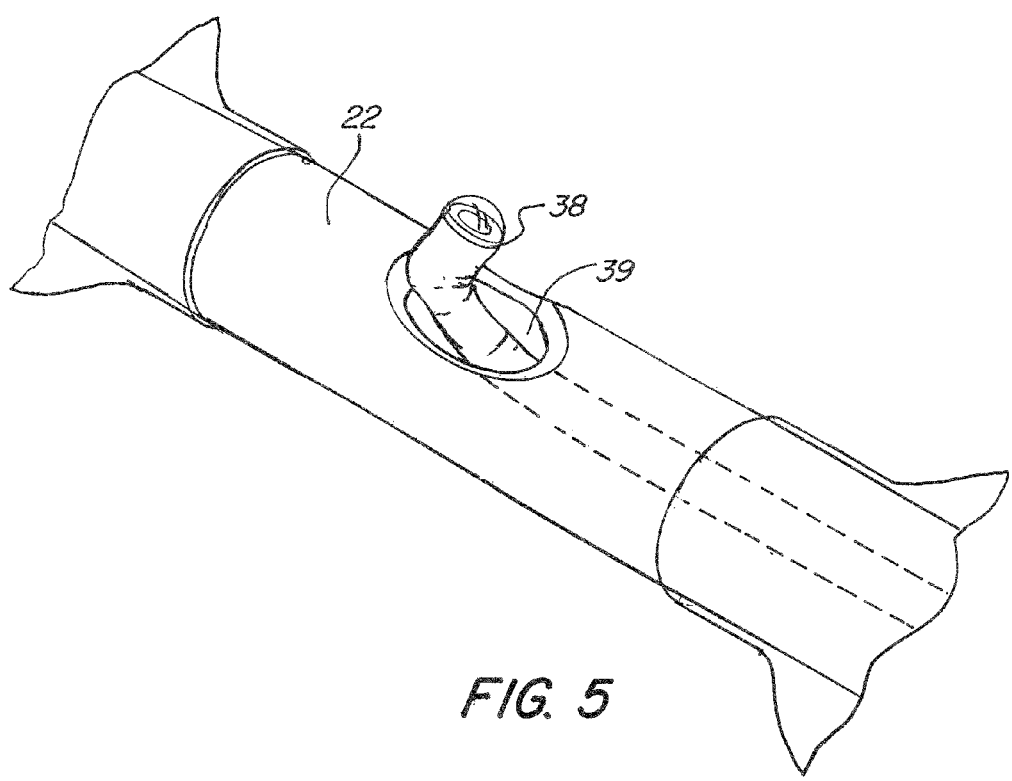
FIG. 5 is an enlarged perspective view of an imaging device of the catheter system of FIG. 1.

The catheter (22) also includes a plurality of lumens, as shown in FIG. 2. The catheter (22) includes two openings (39), one positioned between the first balloon (32) and the third balloon (36), and the other positioned between the second balloon (34) and the third balloon (36), as shown in FIG. 3. The openings (39) are used to supply the therapeutic and/or diagnostic agent via a first lumen (33) of the catheter (22) to tissue in the bodily cavity. It is understood, however, that one opening is sufficient to supply the agent. Additionally, the catheter (22) can include multiple openings positioned on both sides of the third balloon (36) or at any other suitable location along the catheter (22) to supply the agent to different locations in the bodily cavity. In a preferred embodiment, the openings (39) are used to accommodate the imaging device (38) that extends out of the opening (39) such that the surrounding tissue can be viewed by the imaging device (38) during the insertion of the multi-balloon catheter system (20) into the bodily cavity, as shown in FIG. 5.

Referring back to FIGS. 2-3, the third balloon (36) at least partially encloses an inflation chamber (37), which is used to inflate the balloon (36). A second lumen (35) of the catheter is in fluid communication with the inflation chamber (37) via at least one opening (44) in the catheter (22) positioned inside the inflation chamber (37). The second lumen (35) is used to supply fluid from the fluid source (24) to the inflation chamber (37) to inflate the third balloon (36). It should be noted that in some embodiments, the wall of the balloon (36) has at least one opening therein, and the second lumen (35) is used to supply the therapeutic and/or diagnostic agent to the chamber (37), which is then delivered to tissue through the openings in the balloon wall. In these embodiments, the opening(s) in the balloon (36) are very small holes created such that a certain balloon pressure is required in order for them to open up as a result of the expansion and allow the agent to exit through them, thereby permitting the balloon to inflate until the balloon walls are in contact with the cavity wall.

The catheter (22) also includes a third lumen (40) in fluid communication with the first balloon (32) and a fourth lumen (41) in fluid communication with the second balloon (34). The third and fourth lumens (40, 41) supply fluid from the fluid source (24) to the first and second balloons (32, 34) via at least one opening (43, 45) in the catheter (22) positioned inside each of the balloons (32, 34) to inflate the balloons. It should be noted that a single lumen can be provided instead of the two lumens to supply fluid to both first and second balloons (32, 34). Additionally, the outer wall of the balloons (32, 34) can be provided with at least one opening therein, and the lumens (40, 41) are used to deliver the therapeutic and/or diagnostic agent to tissue through the openings in the balloon walls.

The catheter (22) further includes a center lumen (46), which can be used to deliver any number of things to assist insertion and positioning of the multi-balloon catheter system (20) within the bodily cavity and to carry out various medical procedures. It is understood that additional lumens can also be provided in the catheter (22) for introduction of various medical instruments to carry out various diagnostic or therapeutic procedures. The center lumen (46) can also be used as a bypass channel to allow bodily fluids, such as air or blood, to flow through the balloon catheter, which is necessary in certain medical applications, e.g. pulmonology or cardiology. Such a bypass lumen should be large enough to maintain the functionality of the relevant organ (e.g., lungs). In some cases, an external device, such as a respiration device, is in communication with the lumen (46) in order to help facilitate this flow.

Figure 4:
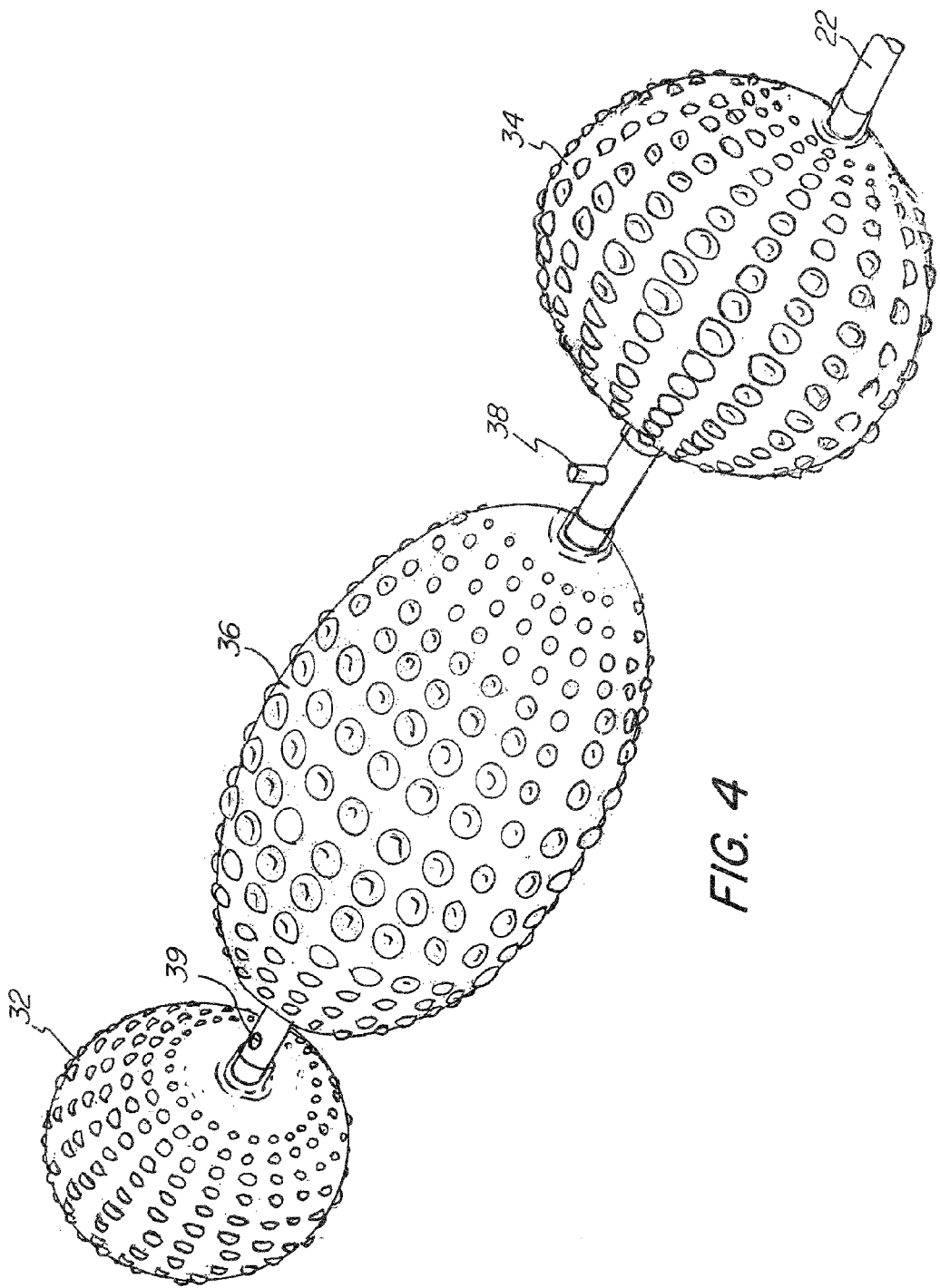
FIG. 4 is an enlarged perspective view of the multi-balloon construct of the catheter system of FIG. 1, showing balloons with textured/abrasive surface.

In an advantageous embodiment shown in FIG. 4, the third balloon (36) has a wall with an outer surface that comprises an abrasive surface intended to abrade bodily tissues, such as airway or vessel walls. The abrasion of the bodily tissues stimulates bleeding and instigates flow of white blood cells, i.e. leukocytes, out of the circulatory system towards the site of tissue damage. This process, together with the application of volumetric pressure or force to the abraded surface of the airway or the vessel wall to neutralize hemodynamic shear forces, perpetuates fluid extravasation processes and stimulates associated cellular absorption of the diagnostic and/or therapeutic agents into the adjacent tissues.

The abrasive outer surface of the third balloon (36) is formed by a fiber mesh affixed to the surface of the balloon during the molding process, which produces outwardly-facing protrusions that optimize the abrasion capability of the balloon (36). The fiber mesh may be made of lycra, polyurethane, nylon, nylon coated with other materials such as cotton, composite springs, or other appropriate material. In other embodiments, dimensional surface structures or inflatable sinuses that are encapsulated in the surface substrate of the balloon (36) may be used to produce the surface protrusions.

In the embodiment shown in FIG. 4, the first and second balloons (32, 34) are provided with a textured surface that assists in gripping of the balloons to the surrounding tissue upon inflation to facilitate secure positioning of the balloons in the bodily cavity. The textured surface of the balloons (32, 34) may be created by the same methods as described above with respect to the third balloon (36).

In certain advantageous embodiments, at least one of the balloons (32, 34, 36) includes imaging markers, such as radio opaque rings, located at or near the ends thereof. Such markers can be selected and appropriately positioned in order to reflect the relevant waves of various imaging modalities (e.g., x-ray) in order to allow the use of such modalities to assist with the precise positioning of the balloons (32, 34, 36) within a bodily cavity. Similarly, the balloon or balloon mesh may include radiopaque material, such as a mesh made of yarn having radiopaque iron fibers.

Figure 6A:
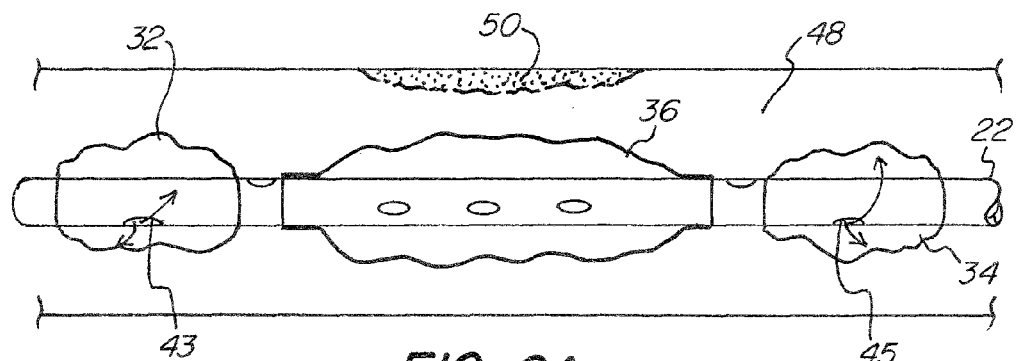
FIGS. 6A-6C are side views of the catheter system of FIG. 1, being operated in a bodily cavity.
Figure 6B:
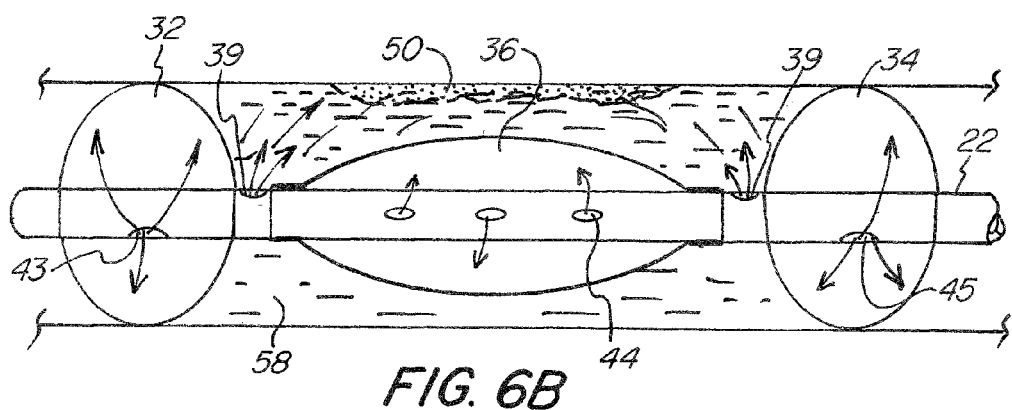
Figure 6C:
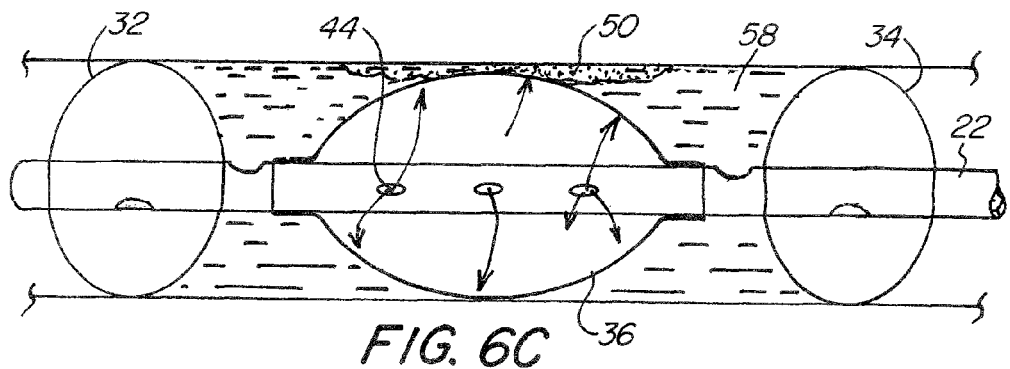

FIGS. 6A-6C illustrate a stepwise operation of the multi-balloon catheter system (20) in a bodily cavity. The catheter assembly (22) is first inserted into a bodily cavity (48) until it is in the vicinity of the target site, which in this case is a tumor (50). As shown in FIG. 6A, once the catheter (22) reaches the desired position in the bodily cavity (48), the first and second balloons (32, 34) are inflated by supplying fluid thereto by the pump (24) via at least one opening (43, 45) positioned inside each of the balloons (32, 34). As shown in FIG. 6B, the balloons (32, 34) are inflated simultaneously to create a chamber therebetween (58), into which the therapeutic and/or diagnostic agents are delivered through the openings (39) in the catheter (22). Alternatively, the first balloon (32) is inflated first and is used as an anchor to secure the balloon catheter assembly (22) at the target site, and then the second balloon (34) is inflated to create the chamber (58).

The chamber (58) functions to isolate the target treatment site from the surrounding tissue, which is particularly desirable during delivery of highly toxic chemotherapy agents to decrease exposure to such agents. Additionally, by creating the fluidly isolated chamber (58), it is possible to change volumetric pressure within the chamber to facilitate extravasation of the agent into target tissue. This can be achieved by repeatedly inflating and deflating the third balloon (32) such that the fluid pressure in the chamber (58) is increased and decreased successively.

As shown in FIG. 6B, once the first and second balloons (32, 34) are inflated to create the chamber (58), the therapeutic and/or diagnostic agent is delivered into the chamber (58) via the openings (39) in the catheter (22). It should be noted that the agent can also be delivered through a plurality of openings provided in one or more of the balloons (32, 34, and 36). As the agent fills the chamber (58), it coats the outer surface of the third balloon (36).

As shown in FIG. 6C, the third balloon (36) is then inflated such that the outer surface of the balloon (36) contacts the tumor tissue (50), and is kept that way for a desired period of time. It should be noted that, although the plurality of openings (44) in the catheter (22) is illustrated in FIGS. 6A-6C, one opening is sufficient to supply fluid to inflate the balloon (36). The balloon (36) is then at least partially deflated, recoated with the agent, re-inflated and kept that way again. This sequential and/or constant expansion of the balloon (36) increases the volumetric pressure within the chamber (58), thereby neutralizing the hemodynamic shear forces, instigating leukocyte extravasation and initiating fluid extravasation through the vessel walls and into the adjacent tissues.

Any of various agents useful in therapeutic application can be delivered in the above described manner. For example, the agent may comprise one or more chemical or biological drugs with useful pharmacological properties, as well as any other medicaments or other substances with medicinal or other therapeutic uses. Such agents may be synthetic or natural, so long as they have an advantageous therapeutic effect that can be obtained by delivering the agent to a target site. In certain embodiments, agents particularly useful for chemotherapies, radiation therapies, or immunotherapies are delivered as described above.

In some advantageous embodiments, a cytotoxic substance or other agent useful for chemotherapy is delivered to a target site via the multi-balloon catheter system of the present invention. For example, in some cases, the catheter system is used to deliver a chemical agent that affects cell division or DNA synthesis. Such agents include, for example, alkylating antineoplastic agents, such as cisplatin, carboplatin, oxaliplatin, mechlorethamine, carmustine, cyclophosphamide, chlorambucil, ifosfamide, busulfan, treosulfan, melphalan hydrochloride, thiotepa, and dacarbazine; anti-metabolites, such as azathioprine, mercaptopurine, thioguanine, fludarabine, pentostatin, cladribine, fluorouracil, floxuridine, cytosine arabinoside, gemcitabine, methotrexate, pemetrexed, and raltitrexed; anthracenedione antineoplastic agents, such as mitoxantrone; anthracyclines, such dactinomycin, daunorubicin, doxorubicin, epirubicin, idarubicin, valrubicin, aclarubicin, and bleomycin; plant alkaloids and terpenoids, such as noscapine, vincristine, vinblastine, vinorelbine, vindesine, podophyllotoxin, paclitaxel, and docetaxel; topoisomerase inhibitors, such as irinotecan, topotecan, amsacrine, etoposide, etoposide phosphate, and teniposide; and other agents with similar mechanisms of action, such as mitomycin C.

Other such agents include those that target molecular abnormalities, including tyrosine kinase inhibitors, such as crizotinib, gefitinib, erlotinib hydrochloride, imatinib, and imatinib mesilate. Still other such agents include those that modulate tumor cell behavior without actually attacking the cells, such as may be employed for hormone treatments. Indeed, any drug known to be efficacious in treating cancerous cells, such as streptozotocin or diltiazem augment taxol, may be employed.

In certain advantageous embodiments, a biological response modifier or other biological agent useful for immunotherapy is delivered to a target site via the multi-balloon catheter system. Such agents, which are often cytokines, may be a recombinant, synthetic, or natural preparation. These biological agents may include, for example, interferons, such as alpha-interferons and beta-interferons; interleukins, such as aldesleukin; colony-stimulating factors, such as filgrastim, sargramostim, epoetin, and oprelvekin; monoclonal antibodies, such as edrecolomab, rituximab, trastuzemab, gemtuzumab, alemtuzumab, nimotuzumab, cetuximab, bevacizumab, ibritumomab, panitumumab, and tositumomab; cancer vaccines; gene therapies; and non-specific immunomodulating agents. Any biologic known to useful for immunotherapies, such as asparaginase, may be employed.

In some advantageous embodiments, the therapeutic agent is delivered in drug eluting microspheres, which can be used both to cause the embolization of blood vessels that supply undesirable tissues and to retain the drug in a localized area for a sustained period of time. For example, drug-eluting microspheres can be used to deliver a chemotherapeutic drug, such as doxorubicin, to a tumor. When the microspheres reach the target site, they will block vessels supplying the tumor, and this suppression of blood flow will lead to ischemia. Over time, the microspheres break down, and the drug will be absorbed by the tissue. As a result, not only is a localized sustained release of the drug achieved, but the ischemia will also increase the effect of the drug on the tumor.

The above described delivery of therapeutic agents is also useful for radiation therapies, in which high-energy radiation is used to kill cancer cells and shrink tumors. One method of such therapy places radioactive material in the body near the cancer cells. Thus, in certain advantageous embodiments, a radioactive substance, such as a radiolabeled monoclonal antibody, is supplied via the multi-balloon catheter and extravasated into nearby tissue as described below.

Various agents may also be employed to assist in making diagnostic observations or monitoring procedures. For example, in some advantageous embodiments, the above described system may be used to deliver a contrast agent that allows or improves visualization via one or imaging modalities, which can be used to image the extravasation of the agent into the surrounding tissues throughout the course of a procedure. Such agents may include, for example, radiocontrast agents, such as iodine or barium, to improve X-ray based imaging techniques; MRI contrast agents, such as gadolinium, to improve magnetic resonance imaging; and microbubble contrast agents, to improve ultrasound imaging.

In some advantageous embodiments, biomarkers are used together with a therapeutic agent to observe and monitor the extravasation of the agent into the surrounding tissues. In some of these advantageous embodiments, CF3PM & MTFN-1 fluorinated radio-opaque biomarkers are used. The biomarkers may be detected by various non-invasive imaging modalities, such as X-Ray, MRI, CT, ultrasound, spectroscopy, etc.

With the addition of an appropriate inert dye or contrast media (e.g., radioactive, polarized, florescent, temperature sensitive) to a drug to be extravasated, the drug infusion rate and the amount of drug infused into the tissue can be monitored, quantified, and recorded/displayed, such as, for example, by capturing and storing sequential video frames under different illumination conditions (UV, IR, polarized, color filters, etc.). Further, by deploying a contrast agent along with a therapeutic agent, one can visually identify the extravasation depths and/or discern the requisite volumetric pressure, force, temperature, frequency and/or time to achieve efficacious delivery of the therapeutic agent to the desired depth of penetration at the intended treatment site.

The multi-balloon catheter system of the present invention can also be used to supply various media, e.g. light based therapies, radiofrequency wave forms, thermal energies and temperatures, and pressured air, to modulate cellular response sufficient to achieve tumoral destruction and to alter cellular membrane integrity to facilitate extravasation of medicinal and/or diagnostic agents into bodily tissues.

Figure 7:
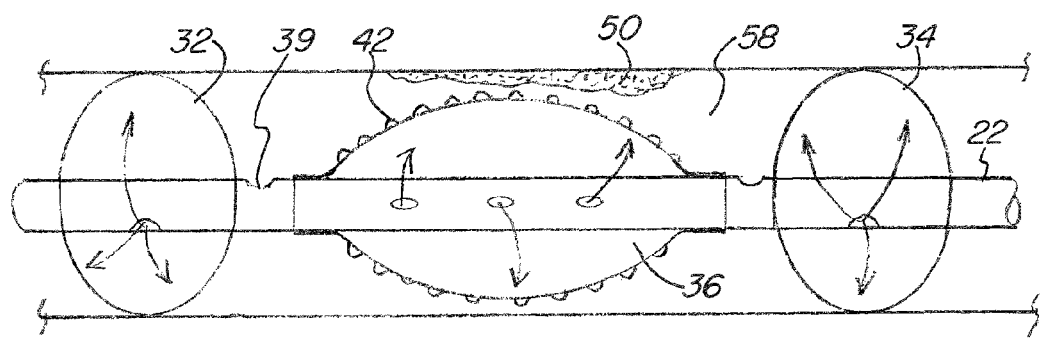
FIG. 7 is a side view of the catheter system of FIG. 1.

Another advantageous embodiment of the multi-balloon catheter system (20) of the present invention is illustrated in FIG. 7. In this embodiment, the wall of the third balloon (36) has an abrasive outer surface (42), as also shown in FIG. 4. As the third balloon (36) becomes inflated, the abrasive outer surface (42) of the balloon comes into contact with surrounding tissue in the bodily cavity and begins to abrade the tissue, thereby prompting bleeding and stimulating a flow of leukocytes to the target tissue site. Then, the third balloon (36) is at least partially deflated and the therapeutic and/or diagnostic agent is supplied to the chamber (58), such that the agent fills the chamber (58). The flow of blood cells caused by the abrasion of the tissue stimulates extravasation and associated cellular absorption of the diagnostic and/or therapeutic agent into the tissue. The third balloon (36) can be sequentially pulsed to create further surface abrasions.

In additional embodiments, the therapeutic and/or diagnostic agent is first delivered via the openings (39) to the chamber (58), such that the agent coats the outer surface (42) of the third balloon (36). Then, the balloon (36) is inflated such that the abrasive surface (42) of the balloon abrades the tissue and stimulates the flow of blood cells, which in turn facilitates absorption of the agent into the tumor tissue (50). When the third balloon (36) is fully inflated, the wall of the balloon is pressed against the tumor tissue (50), which further facilitates the absorption of the therapeutic and/or diagnostic agent into the tissue. Additionally, the inflation of the third balloon (36) can assist in anchoring the balloon within the bodily cavity during the drug delivery process.

In further embodiments, the therapeutic and/or diagnostic agent is also supplied through at least one opening in the wall of the third balloon (36). The balloon (36) is inflated such that the wall of the third balloon (36) presses against the tumor tissue (50), and then the agent is delivered through the openings into the tissue. This way, the agent can be delivered to a more precisely targeted area of the tissue.

Once the agents have been delivered and extravasated into the tissue at the target site, any remaining agents can be evacuated from the chamber (58) via the same openings (39) and lumens through which they were supplied to the chamber (58) using suction. In certain advantageous embodiments, the fluid source (24) produces a negative pressure to vacuum out the agents. Alternatively, additional lumens and corresponding openings may be employed in the manner previously described to evacuate the agents through lumens different from those used to supply the agents to the chamber (58).

In some embodiments, one of the lumens of the catheter (22) is used to supply an irrigation fluid. For example, when using both a therapeutic agent and a contrast agent, once the contrast agent has reached, and sufficiently saturated, the intended treatment site, any remaining contrast agent can be vacuumed out of the chamber (58). The chamber (58) can then be irrigated, lavaged, and suctioned to remove any residual agent.

Figure 8:
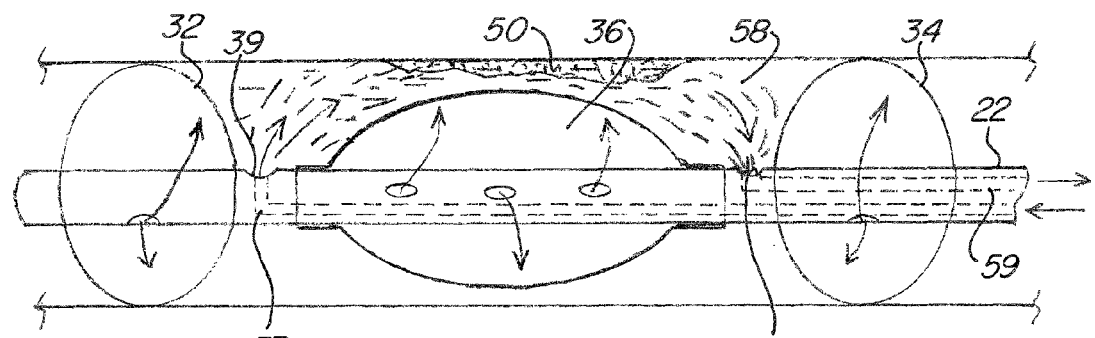
FIG. 8 is a side view of the catheter system of FIG. 1.

In an advantageous embodiment, the various lumens and corresponding openings can be used to cyclically deliver and evacuate the agents and various other fluids instantly, sequentially, intermittently and/or continuously over designated time intervals. For example, as shown in FIG. 8, the catheter (22) includes a lumen (33) through which the therapeutic and/or diagnostic agent is supplied to the chamber (58) via an opening (39) in the catheter, and a further lumen (59) through which the agent is evacuated from the chamber (58) via an opening (73) in the catheter. This way, the agent is circulated within the chamber (58), which allows for a better extravasation of the agent into the surrounding tissue.

In certain embodiments, the catheter (22) has multiple lumens to supply therapeutic agents to the target tissue, which allows for delivery of multiple agents separately, as may be desired when using two different pharmaceuticals that should not be mixed until just before being extravasated into bodily tissue. For example, the catheter (22) can include two delivery lumens, each supplying a different agent via a separate opening in the catheter. Likewise, one may need to deliver one medicinal agent at the beginning of the procedure, and another medicinal agent at a later time during the procedure. Furthermore, one may wish to deliver a second agent at a slightly different location than the first agent, which can be accomplished by providing two separate openings in the catheter (22), for example one at the distal end of the third balloon (36) and the other at the proximal end of the third balloon (36), and delivering each agent to tissue adjacent to each of the openings.

In an advantageous embodiment, an imaging device (38) disposed in one of the lumens of the catheter (22) is used to help position the balloon system at the proper location. For example, the lumen (33) that delivers the therapeutic and/or diagnostic agent may be large enough to also accommodate the imaging device (38), such that the imaging device can exit one of the openings (39), through which the agent is delivered to tissue. Preferably, the imaging device (38) extends out of the opening (39) in the catheter (22), as shown in FIG. 5, such that the tissue in front of the catheter can be viewed by the imaging device during the insertion of the multi-balloon catheter (20) into a bodily cavity.

In other embodiments, the wall of at least one of the balloons (32, 34, 36) is transparent, and the imaging device (38) is introduced via one of the catheter lumens (35, 37, 41), through which fluid is supplied to the balloons (32, 34, 36), and is extended out of one of the openings (43, 44, 45) in order to view the surrounding area through the transparent wall of the balloons. Alternatively, an additional lumen can be provided in the catheter (22) to accommodate the imaging device (38), such as the center lumen (46), and this lumen can connect to an opening leading to the inside of the balloons (32, 34, 36) or to one of the openings (39) in the catheter outside the balloons.

In some advantageous embodiments, the distal end of the catheter (22) includes a transparent membrane made out of any suitable material. The imaging device (38) is extended through one of the lumens of the catheter to the membrane, which allows for visualization of the area ahead of the catheter (22). In this way, the physician can be provided with illuminated light and direct visual feedback of the area ahead of the balloon catheter, along the sides of the balloons, and/or behind the balloons.

In other advantageous embodiments, the lumen of the catheter (22), in which the imaging device is disposed, has an opening at a distal end, and the imaging device is extended out of the opening to visualize tissue in front of the multi-balloon catheter system (20). In this embodiment, the catheter (22) can also be provided with a cleaning device at the distal tip for cleaning the imaging device (38). The cleaning device is made with any suitable type of material, such as textile bundle, and is affixed to an inner surface of the catheter (22) adjacent to the opening at the distal end. The imaging device is cleaned by moving it back and forth through the textile bundle, thus wiping a lens of the imaging device.

The imaging device (38) can be any device suitable for viewing the target area, such as a coherent fiber bundle or appropriate optical element and lens assembly in conjunction with an imaging sensor (e.g., CMOS, CCD), having a sufficiently small outer diameters, such as, for example, 0.75 mm-1.2 mm. In some cases, the imaging device has a pre-shaped distal tip that enables it to easily extend through one of the aforementioned openings. The distal tip of the imaging device is preferably flexible such that it can be translated linearly or rotationally thereby allowing for 360° visualization of the surrounding area.

Figure 9:
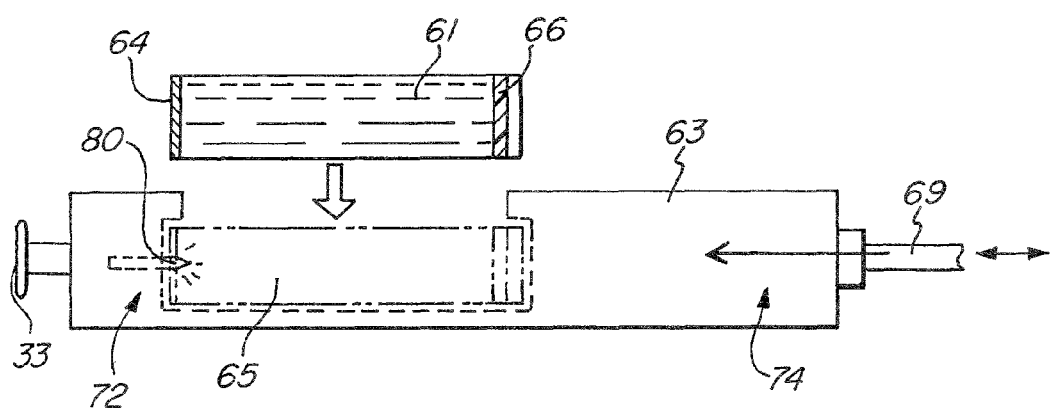
FIG. 9 is a side view of a delivery mechanism of the catheter system of FIG. 1.

The therapeutic and/or diagnostic agent can be delivered to the lumen (33) via any suitable mechanism. In one advantageous embodiment shown in FIG. 9, the therapeutic and/or diagnostic agent is contained in a drug capsule (61) adapted to be positioned into a delivery apparatus (63). The drug capsule (61) is prefilled with the agent and is sealed at a distal end by a pierceable membrane (64) and at a proximal end by a slidable piston (66). The capsule (61) can be made out of any suitable material, and preferably is transparent such that the amount of the agent delivered can be monitored. The size of the drug capsule (61) and the amount of the agent it can hold can be variable depending on a particular application. For example, the capsule (61) can be filled with the amount of the agent to be delivered plus the amount needed to prime the drug delivery lumen (33) of the catheter (22). The drug delivery lumen (33) can also be primed before the catheter (22) is deployed to the target area.

The drug capsule (61) fits into a capsule compartment (65) of the delivery apparatus (63), which is connected to the delivery lumen (33) at a distal end (72) and is connected to a fluid source at a proximal end (74) via a lumen (69). The fluid source can be the same pump that is used to inflate the inner balloon or can be a separate pump. The distal end (72) of the capsule compartment has a needle (80) or any other suitable piercing device that functions to pierce the membrane (64) of the capsule (61). The proximal end (74) of the capsule compartment has an actuation mechanism adapted to actuate the piston (66) of the capsule (61). The capsule compartment (65) is preferably made out of transparent material such that the location of the piston can be determined and therefore the amount of the agent delivered can be observed and monitored.

The capsule (61) filled with the therapeutic and/or diagnostic agent is first positioned into the capsule compartment (65) of the delivery apparatus (63), such that the membrane (64) is pierced by the needle (80) located at the distal end (72) of the capsule compartment (65) to allow the agent to exit out towards the delivery lumen (33). Once the drug capsule (61) is securely positioned inside the capsule compartment (65), the actuation mechanism actuates the piston (66) such that it moves towards the distal end of the capsule (61), ejecting the therapeutic and/or diagnostic agent out of the capsule into the delivery lumen (33) of the catheter (22). If the agent to be delivered to tissue is in gaseous form, the delivery apparatus (63) can further include a valve (not shown) positioned at the distal end of the apparatus before the connection to the drug delivery lumen (33). The valve controls how much gaseous agent is delivered to the lumen (33), as well as the delivery time.

The actuator mechanism of the delivery apparatus (63) can be a pneumatic cylinder, into which fluid is supplied by the fluid source, wherein fluid pressure pushes the piston (66) forward, ejecting the agent out of the capsule (61). In other embodiments, the actuator mechanism can be an electrical motor, e.g. a stepper motor or a servo motor. The actuator mechanism (63) is connected to a controller that controls the quantity of the agent to be delivered and the delivery time period. The controller can be pre-programmed to deliver the exact quantity of drug over the exact amount of time, or it can be operated manually by the user during the procedure.

The piston (66) is preferably provided with a sensor, e.g. a magnetic sensor, optical or mechanical encoder, or any other suitable type of sensor, so that the position of the piston can be detected and communicated to the controller, which then determines how much drug has been delivered. A pressure transducer can also be provided at the distal end of the delivery apparatus (63) for measuring pressure in the drug delivery lumen (33) and reporting it to the controller that regulates the drug delivery rate and detects any problems that may arise. The controller also regulates and modulates the inflation and deflation of the inner balloon.

It should be noted that other embodiments of the drug delivery mechanism can be used without departing from the spirit of the present invention. The drug capsule prefilled with the agent to be delivered can be primed at any location along the catheter (22), such as, for example, adjacent to the balloon (32). The capsule can be disposed in the outer housing of the catheter or in any of the catheter lumens.

Figure 10A:
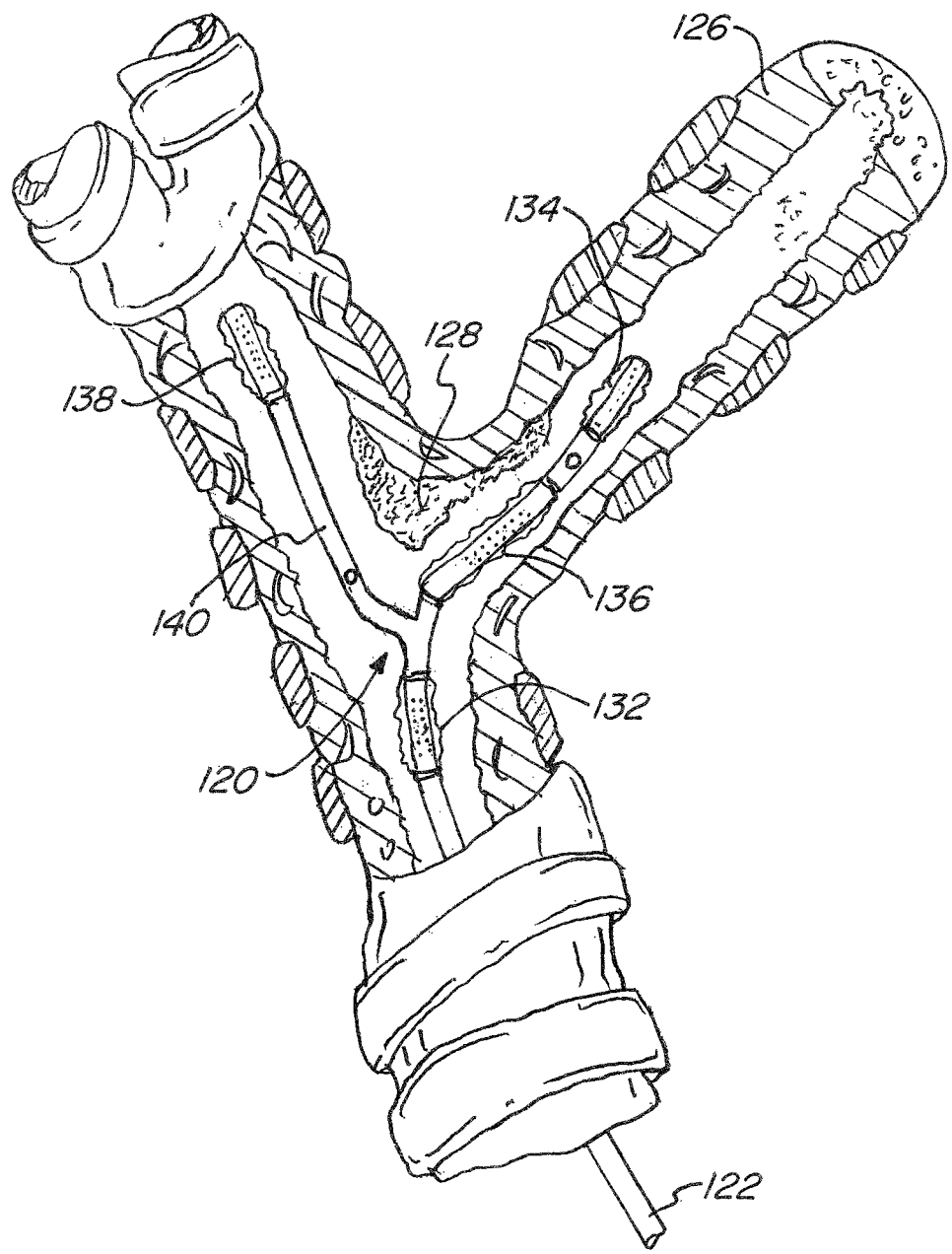
FIGS. 10A-10C are partially exposed, isometric views of the catheter system of FIG. 1 with a four-balloon construct, being operated in a bodily cavity.
Figure 10B:
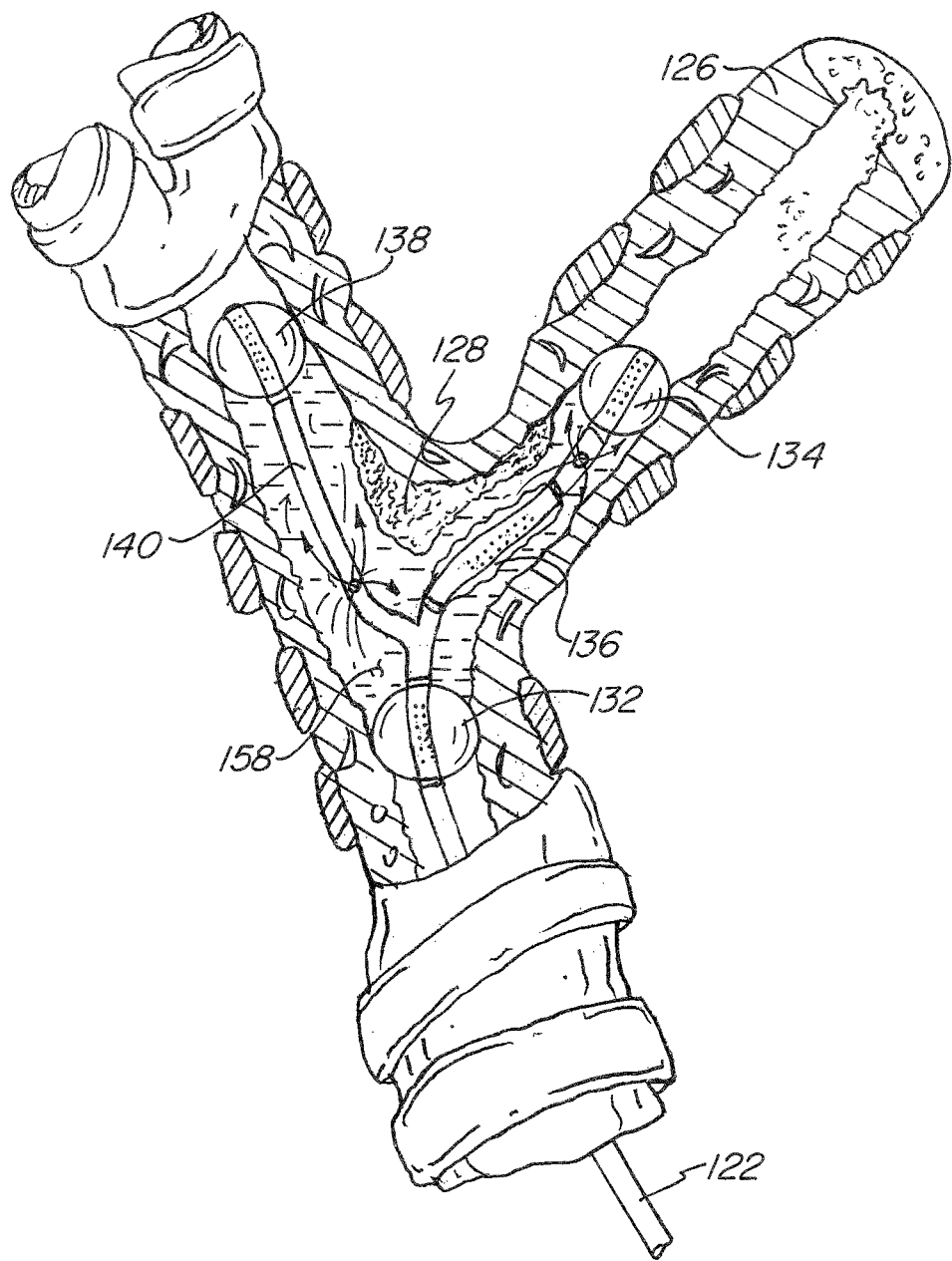
Figure 10C:
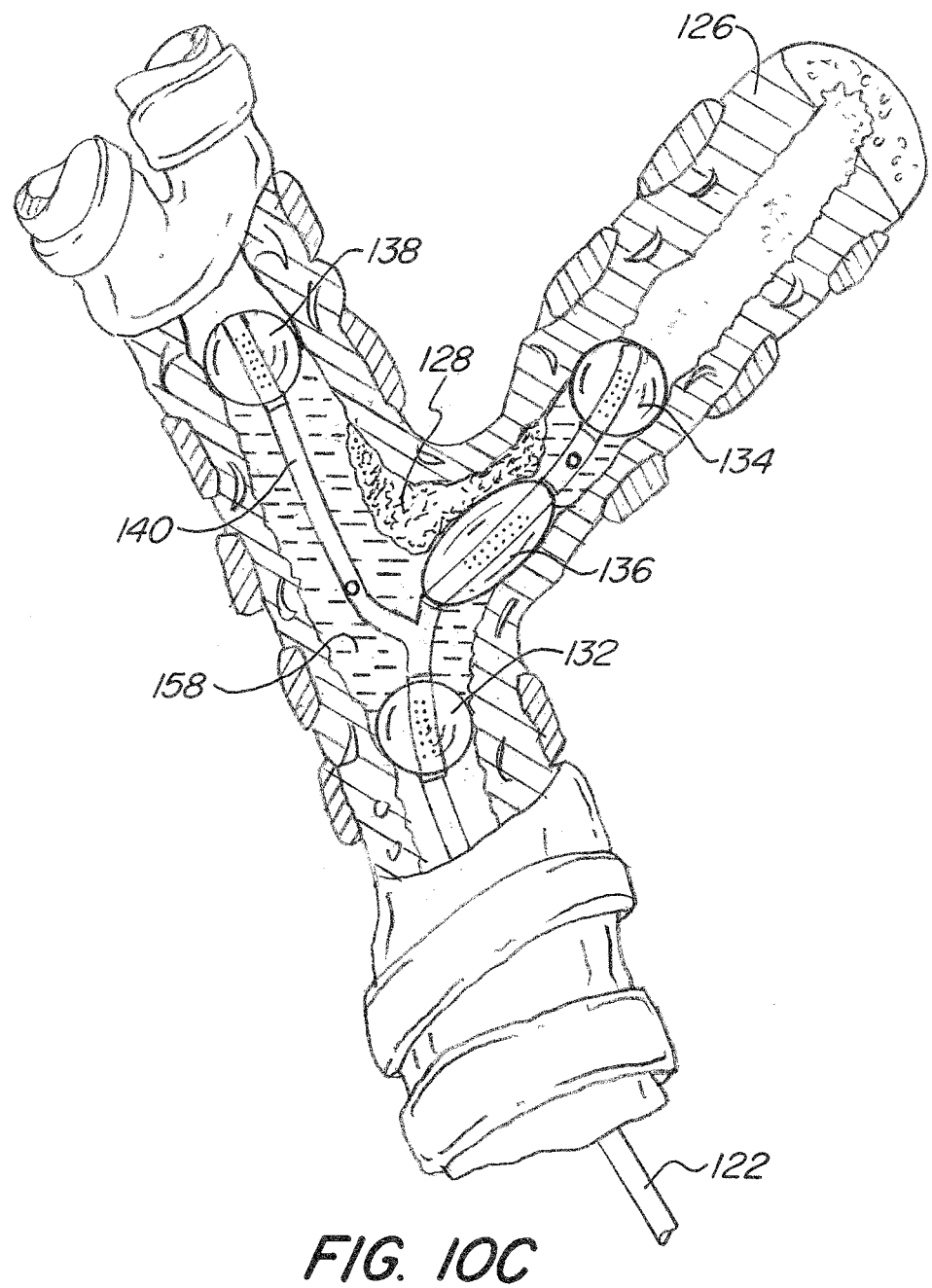

FIGS. 10A-10C illustrate another advantageous embodiment of the multi-balloon catheter system of the present invention. In this embodiment, the multi-balloon catheter system (120) includes a catheter (122) and four inflatable balloons (132, 134, 136, 138) positioned at a distal end of the catheter (122). This embodiment is particularly advantageous for use in branched bodily lumens, wherein a target tissue site, such as a tumor (128), is positioned at a Y-junction of the bodily lumen (26). As shown in FIG. 10A, the catheter (122) has a first balloon (132), a second balloon (134) and a third balloon (136), positioned between the first and second balloons (132, 134). The catheter further includes a fourth balloon (138) connected to the catheter (122) through an additional catheter section (140). The catheter section (140) is coupled to the main catheter (122) at a connection point positioned between the first balloon (132) and the third balloon (136). It is understood that the catheter section (140) can also be connected to the catheter (122) at any other suitable position along the catheter.

The catheter section (140) includes at least one fluid passageway for supplying fluid to the fourth balloon (138) from the fluid source (24) to inflate the balloon. The fluid is supplied via a plurality of openings in the catheter section (140) positioned inside the balloon (138). The fluid passageway is connected to one or both of the lumens (40, 41) in the catheter (22) that are used to supply fluid to the first and second balloons (32, 34). It is understood, however, that the fluid passageway can be separate from the lumens (40, 41) to allow for independent inflation of the balloon (138).

In some embodiments, the catheter section (140) includes additional passageways for delivering any number of things to assist insertion and positioning of the multi-balloon catheter system (120) within the bodily cavity and to carry out various medical procedures. For example, additional passageways can be used to introduce an imaging device for visualizing the surrounding tissue to facilitate insertion of the catheter system into the bodily cavity. The additional passageways can also be used to introduce various medical instruments to carry out various diagnostic or therapeutic procedures, and/or can be used as a bypass channel to allow bodily fluids, such as air or blood, to flow through the balloon catheter. The catheter section (140) can also include a passageway for supplying the therapeutic and/or diagnostic agents to the surrounding tissue. The agents can be supplied via one or more openings along the catheter section (140) and/or via openings in the outer wall of the fourth balloon (138).

In an advantageous embodiment, the fourth balloon (138) is provided with a textured outer surface that assists in gripping of the balloon to the surrounding tissue upon inflation to facilitate secure positioning of the balloons in the bodily cavity. The textured surface of the balloon (138) may be created by the same methods as described above with respect to the other balloons (32, 34, 36).

As shown in FIG. 10A, the four-balloon catheter assembly is first introduced into the bodily cavity (126), with all four balloons (132, 134, 136, 138) in a deflated state. The second balloon (134) is guided to one of the branches of the bodily cavity (126) until it reaches the target site. The fourth balloon (138) is similarly guided to the other branch of the bodily cavity. The insertion of the catheter assembly is preferably facilitated by imaging devices positioned adjacent to the second and fourth balloons (134, 138) to view tissue in front of each of the balloons (134, 138).

Next, the second and fourth balloons (134, 138) are inflated by supplying fluid thereto from the fluid source (24) to anchor the multi-balloon catheter system in the bodily cavity (126), as shown in FIG. 10B. The first balloon (132) is then inflated to form an isolated chamber (158). As discussed above, the chamber (158) functions to isolate the target treatment site from the surrounding tissue, which is particularly desirable during delivery of highly toxic chemotherapy agents to decrease exposure to such agents. Additionally, by creating the fluidly isolated chamber (158), it is possible to change volumetric pressure within the chamber to facilitate extravasation of the agent into target tissue.

Then, the therapeutic and/or diagnostic agent is delivered into the chamber (158) via openings in the catheter (122) and/or the catheter section (140), as shown in FIG. 10B. It is understood that the agent can also be delivered through a plurality of openings provided in one or more of the balloons (132, 134, 136, 138). The third balloon (136) is then inflated, as shown in FIG. 10C, such that the outer surface of the balloon contacts the tumor tissue (128), and is kept that way for a desired period of time. The balloon (136) can also be sequentially and/or constantly expanded to increase the volumetric pressure within the chamber (158), thereby neutralizing the hemodynamic shear forces, instigating leukocyte extravasation and initiating fluid extravasation through the vessel walls and into the adjacent tissues.

Figure 11A:
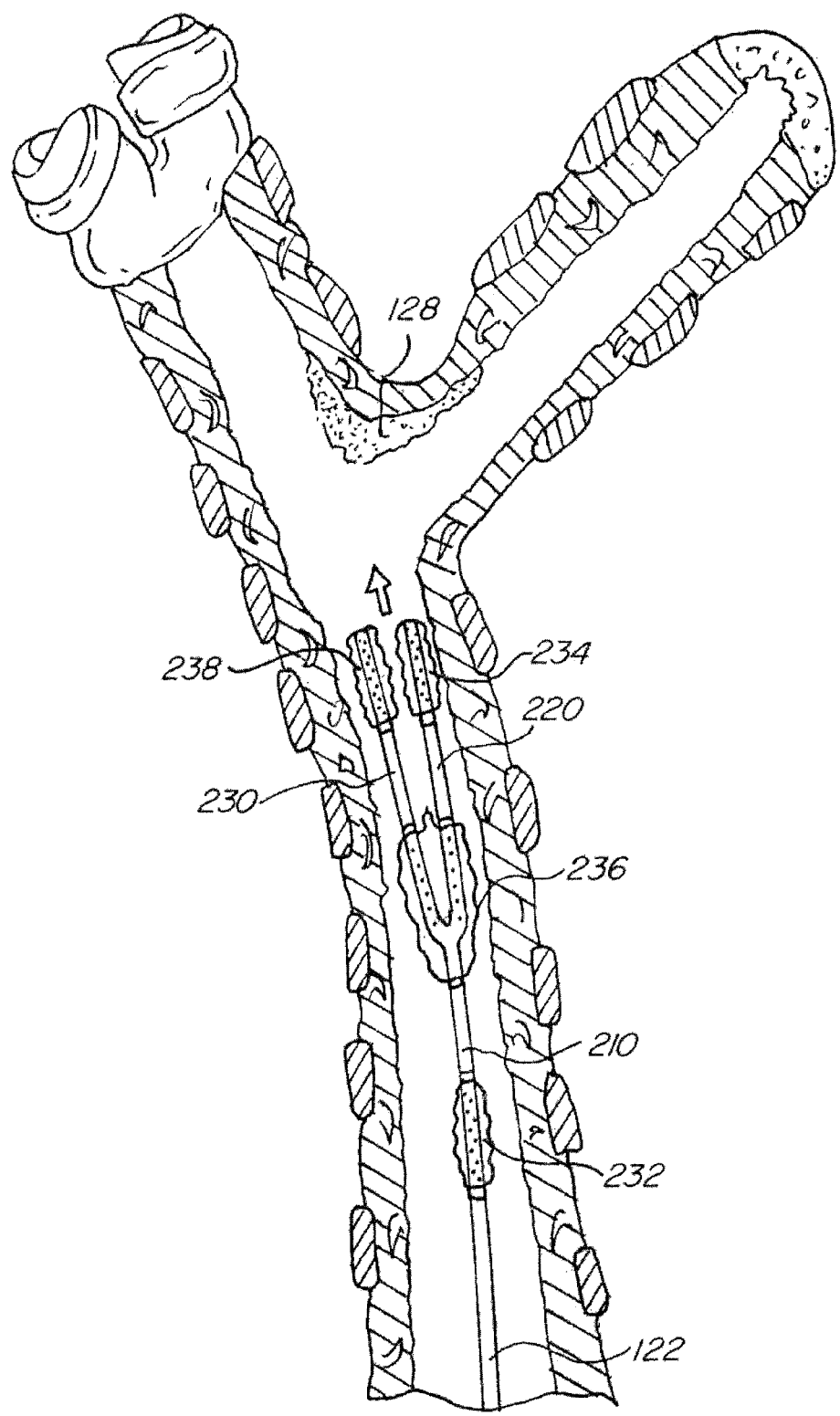
FIGS. 11A-B are partially exposed, isometric views of the catheter system of FIG. 1 with a four-balloon construct, being deployed in a bodily cavity.
Figure 11B:
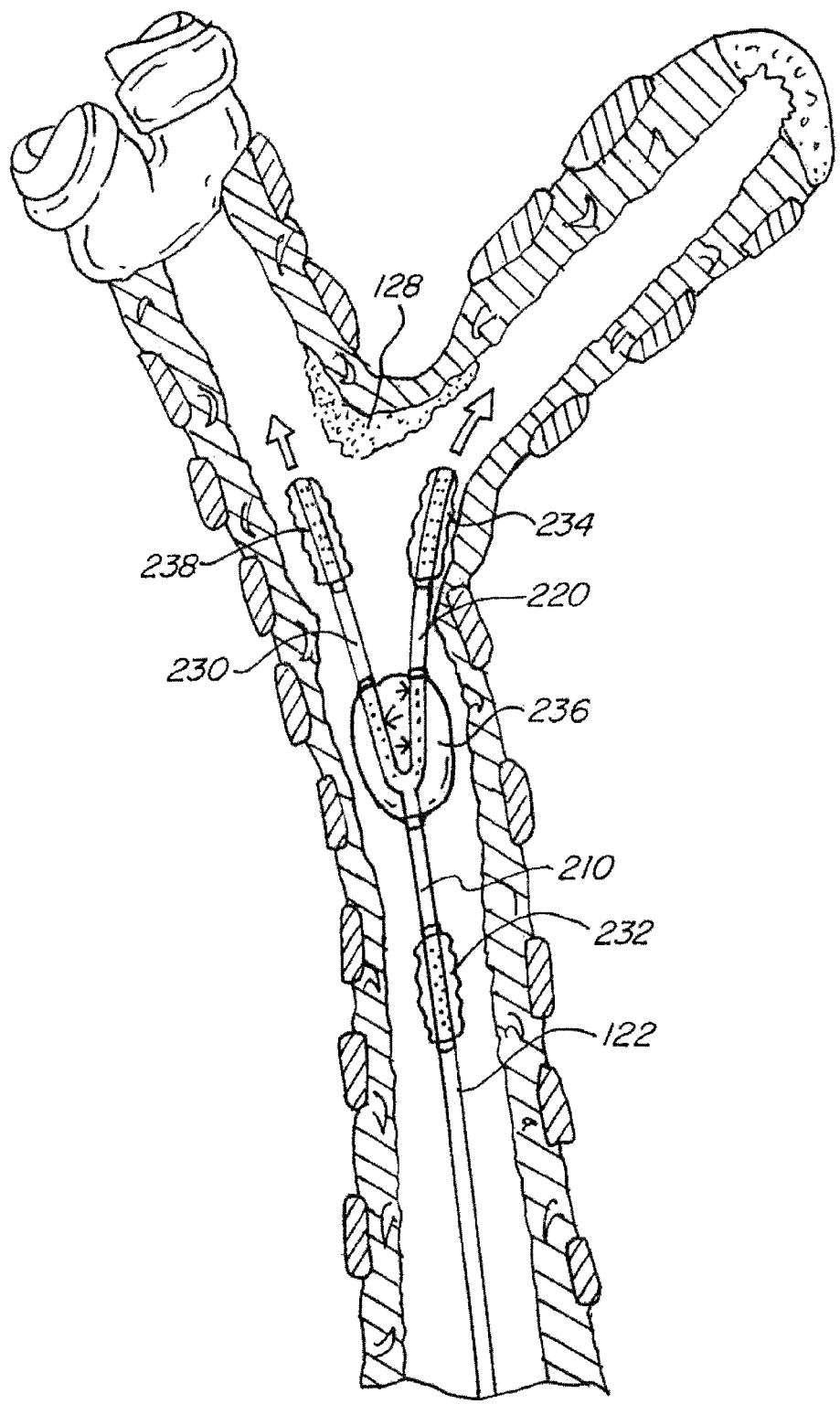

As shown in FIGS. 11A-B, in some embodiments, the third balloon is located at the Y-junction of the catheter (122), which may assist the resection of a tumor that is located across the junction of two different branches of the bodily cavity (126).

As shown in FIG. 11A, the catheter (122) includes a first catheter section (210) connecting the first balloon (232) and the third balloon (236), a second catheter section (220) connecting the second balloon (234) and the third balloon (236), and a third catheter section (230) connecting the fourth balloon (238) and the third balloon (236). When the catheter is first deployed, the second and third catheter sections (234, 238) are fairly close together. Typically, when initially inserted, the catheter (122) will be advanced through a cannula or the working channel of an endoscope so that the Y-shape of the second and third catheter sections (220, 230) does not cause one or both of these sections to snag on the wall of the bodily cavity.

As shown in FIG. 11B, when the catheter (122) is advanced through the bodily cavity and the second and fourth balloons (234, 238) approach the Y-junction of that cavity, the third balloon (236) is partially inflated in order to push the second and third catheter sections (220, 230) further away from each other. In this way, the catheter sections (220, 230) are guided into the separate branches of the bodily cavity.

It should be noted that a fifth balloon (not shown), similar to the third balloon (136), can be located on the third catheter section (230), such that the aforementioned extravasation and/or abrasion can be achieved in multiple branches of the bodily cavity at the same time. It should also be noted that, alternatively, the catheter (122) may include only the first, second, and third balloons (232, 234, 236), and a separate catheter can be used to deploy the fourth balloon (238) (and possible fifth balloon) into the other branch of the bodily cavity.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method of extravasated delivery of a therapeutic and/or diagnostic agent to tissue, comprising the steps of:
   inserting a catheter into a bodily cavity, said catheter comprising
   a first balloon;
   a second balloon; and
   a third balloon positioned between said first and second balloons;
   inflating said first and second balloons to create a chamber between the first balloon and the second balloon, wherein the boundaries of said chamber are defined by an inner surface of the cavity wall and the catheter;
   delivering the therapeutic and/or diagnostic agent to the chamber; and
   facilitating extravasation of the agent inside said chamber and external of the third balloon into tissue by repeatedly increasing and decreasing fluid pressure within the chamber by repeatedly at least partially inflating and at least partially deflating the third balloon in pulsed fashion.

2. A method of extravasated delivery of a therapeutic and/or diagnostic agent to tissue, comprising the steps of:
   inserting a catheter into a bodily cavity, said catheter comprising
   a first balloon;
   a second balloon;
   a third balloon positioned between said first and second balloons; and
   a fourth balloon;
   inflating said first, second, and fourth balloons by supplying fluid thereto to create a chamber between the first balloon, the second balloon and the fourth balloon, and to secure the catheter in the bodily cavity;
   wherein the catheter includes a first catheter section connecting the first balloon and the third balloon, a second catheter section connecting the second balloon and the third balloon, and a third catheter section connecting the fourth balloon and the third balloon, wherein the first, second, and third catheter sections are interconnected inside the third balloon.

3. The method of claim 2, wherein the step of inserting the catheter into the bodily cavity includes increasing a distance between the second and third catheter sections by at least partially inflating the third balloon to insert the second and third catheter sections into different portions of the bodily cavity.

4. The method of claim 1, wherein the third balloon has a wall with an abrasive outer surface, and wherein the method further includes the step of abrading tissue in the bodily cavity by contacting the tissue with the abrasive surface when the third balloon is inflated.

5. The method of claim 1, wherein the first balloon and the second balloon each have a wall with a textured outer surface, and wherein the step of inflating the first and second balloons further comprises contacting tissue in the bodily cavity with the textured surface to prevent slippage of the surface on the tissue.

6. The method of claim 1, further comprising monitoring at least one vital sign of a patient.

7. The method of claim 1, further comprising the step of circulating the therapeutic and/or diagnostic agent within the chamber, wherein the agent enters the chamber through a first opening in the catheter positioned on one side of the third balloon and exits the chamber through a second opening in the catheter positioned on the other side of the third balloon.

8. The method of claim 1, further comprising the step of using an imaging device disposed in the catheter to visualize tissue in the bodily cavity.

9. The method of claim 1, further comprising the step of measuring at least one characteristic of tissue in the bodily cavity via at least one sensor.

10. The method of claim 1, wherein the agent is doxorubicin.

11. The method of claim 1, wherein the agent is cisplatin, and wherein the method further comprises the step of supplying a second agent, said second agent being epinephrine.

12. The method of claim 1, wherein the agent is 5-4 fluorouracil.

13. The method of claim 1, wherein the agent is noscapine.

14. The method of claim 1, wherein the agent is diltiazem augment taxol.

15. The method of claim 1, wherein the agent is crizotinib.

16. The method of claim 1, wherein the agent is erlotinib hydrochloride.

17. The method of claim 1, wherein the agent is gefitinib.

18. The method of claim 1, wherein the agent comprises drug eluting microspheres.

19. The method of claim 1, wherein the agent is a combination of at least one therapeutic agent and at least one biomarker, and wherein the method further comprises the step of monitoring extravasation of the at least one therapeutic agent into tissue via the at least one biomarker.

20. The method of claim 1, wherein a distal end of the catheter has an opening therein, and wherein the method further comprises the step of passing bodily fluids through a lumen in the catheter via the opening.

21. The method of claim 4, wherein said abrasive outer surface comprises a fiber mesh disposed on the wall of the third balloon.

22. The method of claim 5, wherein said textured outer surface comprises a fiber mesh disposed on the wall of the first and second balloons.

23. The method of claim 1, further comprising the step of measuring a patient's blood pressure.

24. The method of claim 23, wherein the step of repeatedly at least partially inflating and at least partially deflating the third balloon in pulsed fashion is based at least in part on the measured blood pressure.

* * * * *